(12) United States Patent
Rogers et al.

(10) Patent No.: US 10,410,503 B2
(45) Date of Patent: Sep. 10, 2019

(54) MOISTURE DETECTION SYSTEM

(71) Applicants: Gerald Rogers, Dallas, TX (US);
Fahim Shaikh, Garland, TX (US)

(72) Inventors: Gerald Rogers, Dallas, TX (US);
Fahim Shaikh, Garland, TX (US)

(*) Notice: Subject to any disclaimer, the term of this patent is extended or adjusted under 35 U.S.C. 154(b) by 0 days.

(21) Appl. No.: 15/932,005

(22) Filed: Jan. 23, 2018

(65) Prior Publication Data
US 2019/0228638 A1    Jul. 25, 2019

(51) Int. Cl.
*G08B 21/20*    (2006.01)
*G01N 27/04*    (2006.01)
*G08B 29/04*    (2006.01)
*G08B 25/10*    (2006.01)

(52) U.S. Cl.
CPC .......... *G08B 21/20* (2013.01); *G01N 27/048* (2013.01); *G08B 25/10* (2013.01); *G08B 29/04* (2013.01)

(58) Field of Classification Search
CPC ......... A61F 13/42; G08B 21/20; G08B 25/10; G08B 29/04; G01N 27/048
See application file for complete search history.

(56) References Cited

U.S. PATENT DOCUMENTS

2015/0130637 A1*  5/2015  Sengstaken, Jr. ...... G08C 17/02
                                                                      340/870.16
2017/0098044 A1*  4/2017  Lai ..................... G06K 19/0716

* cited by examiner

*Primary Examiner* — Omeed Alizada

(57) ABSTRACT

Wireless moisture detection system using water soluble insulated wire or water soluble conductors as sensor inputs to a programmed microcontroller to determine if the water soluble sensors have been penetrated by moisture dissolving the soluble materials and changing the electrical characteristics of the sensor providing an interrupt to the microcontroller to signal the presence of moisture for the monitor to wirelessly communicate to the monitoring system.

2 Claims, 5 Drawing Sheets

Moisture Sensor WSC

Wireless Moisture Monitor

MOISTURE DETECTION SYSTEM

FIELD OF THE INVENTION

The present invention is generally related to devices and methods for detecting moisture. More particularly, the invention relates to electronic components with changing electrical characteristics when exposed to moisture and attached to electronic circuit capable of identifying and signaling the change in the electronic components characteristics indicating the presence of moisture.

BACKGROUND OF THE INVENTION

Moisture detectors are used in a variety of applications using resistance or capacitance or a combination of the two. Resistance of a material is proportional to the amount of moisture in the material measured by inserting two probes in the material and measuring the resistance between the probes. Planar capacitor configurations can measure the change in capacitance due to the change in relative permittivity as a function of the moisture content in the material under test.

Advances in technology and in particular Radio-Frequency IDentification (RFID) for detecting moisture in material has significantly reduced the cost and size of moisture sensors. RFID tag incorporating a tag IC connected to an antenna attaches to the material under test. The reader activates the tag IC transmitting radio-frequency (RF) at the tag antenna and the tag circuit connected to the antenna converts the RF into a DC power for powering the IC and communicating back to the reader. The relative permittivity of the antenna changes with the changing moisture content which is communicated to the reader and used to signal moisture content.

RFID sensor tags do not require any batteries in order to operate, receiving power from the RF transmitted from a reader to power and signal a tag to respond. Reading distance is a function of the reader's transmitted power, tag antenna size, any electrical obstruction, and orientation of tag antennas relative to the reader transmitting antenna. Tag reading distance and reliability due to the issues mentioned, is a problem for many applications.

SUMMARY OF INVENTION

A preferred embodiment uses a water soluble insulating coating on a conductive material such as, but not limited to, a stainless steel wire, silver wire or carbon fiber. A bare wire twined together with a soluble insulated coated wire (twisted pair) and one end of each attached to a monitoring device detecting the current flow through the two conductive fibers or wires. The twisted pair comes in contact with moisture and the insulting coating dissolves resulting in the twisted wires shorting (touching) increasing the current flow between the wires signaling a moisture alarm.

Another embodiment incorporates water soluble materials doped with conductive material such as, but not limited to, carbon nano tubes or silver micro flakes, fabricating a moisture soluble conductor. The water soluble conductive material can be deposited on a substrate such as a cardboard container, metal, plastic or wood and fastened to a wire connector for attaching to a electrical moisture sensor for signaling moisture penetration of the substrate. Water soluble conductor can be molded into a flexible rod similar to a wire and used to detect the presence of moisture when attached to an electric moisture sensor. The water soluble conductive rod provides the user with flexibility to use the disposable sensor with electrical sensor monitors in most spaces where water detection is required.

DETAIL DESCRIPTION OF THE INVENTION

In the following description, the various embodiments of the present invention will be described in detail. However, such details are included to facilitate understanding of the invention and to describe the preferred embodiment of the invention. Such details should not be used to limit the invention to the particular embodiments described because other variations and embodiments are possible while staying within the scope of the invention. Furthermore, although numerous details are set forth in order to provide a thorough understanding of the invention, it will be apparent to one skilled in the art that these specific details are not required to practice the invention. In other instances, details such as well-known methods, electrical circuit, processes, program, and interfaces are illustrated in block diagram form so as to not obscure the present invention.

Figure 1:
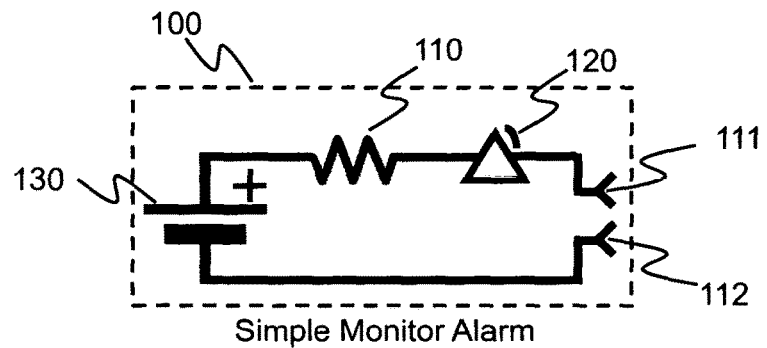
FIG. 1 is a simple monitor alarm detects current flow from terminal 111 to terminal 112.

FIG. 1 is a circuit schematic for a monitor incorporating an alarm 120 indicator to present to the user the status of connectors 111 and 112 open circuit or high resistance with no current or not enough current flowing through alarm 120 for activation. Alarm 120 can be a LED, vibration motor, piezoelectric buzzer or magnetic buzzer or any electric component to provide audio visual alerts. Connectors 111 and 112 shorted together or low resistance connection will have current flowing through the alarm resulting in audio, visual and/or vibration from the alarm limited by resistor 110.

Figure 2A:
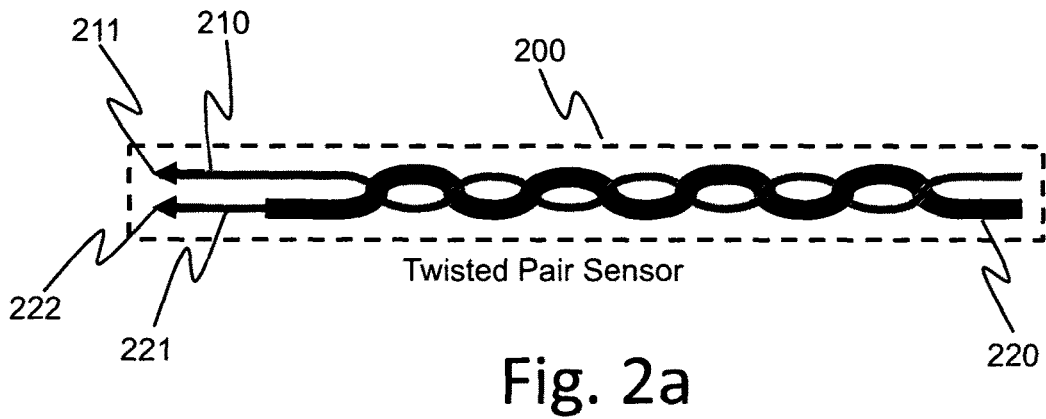
FIG. 2a is water soluble insulation coated wire twisted together.

FIG. 2a is a moisture sensor using a wire coated with water soluble insulation 220 intertwined with a bare wire 210 forming twisted pair 200. Wire 220 has the water soluble insulation removed or stripped away to expose bare wire to attach to connector 222 and wire 210 is attached to connector 211. Water soluble insulation material such as polyvinyl alcohol or polyethylene glycol can be used as a water soluble insulation for coating a conductor.

Figure 3A:
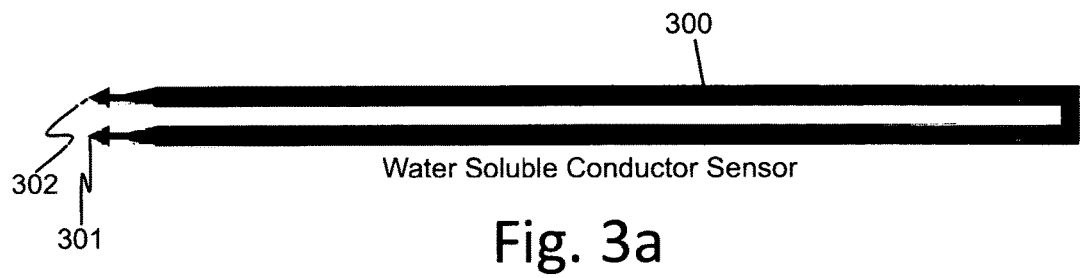
FIG. 3a is a water soluble electric conductor using a soluble material doped with carbon or metal such as silver for conductivity.

Referring to FIG. 3a, another configuration of a moisture sensor is a water soluble synthetic conductor fabricated by doping or mixing a conductive material such as carbon micro tubes or sliver micro flakes in a water soluble material such as polyvinyl alcohol. Electrical connectors 302 and 301 are integrated into the conductor for mating with connectors 111 and 112 of simple monitor alarm 100.

One skilled in the art having read the description of this invention would understand there are numerous ways to design moisture sensors using water soluble materials. Such as, fabricating moisture sensors with water soluble insulation material sandwiched between two conductive materials with each conductive material attached to a connector to mate with a monitor to measure the conductivity between the materials. Soluble insulation can be a film spread between the conductive fabrics or deposited on one of the conductive fabrics with the other spread over the coating of the first conductive fabric creating a sandwiched fabric with insulation separating the two fabrics. The conductive fabrics and materials are porous allowing moisture to permeate and dissolve the water soluble insulation resulting in the two materials or fabrics to short together changing the resistance from an open circuit to a short circuit.

Figure 4:
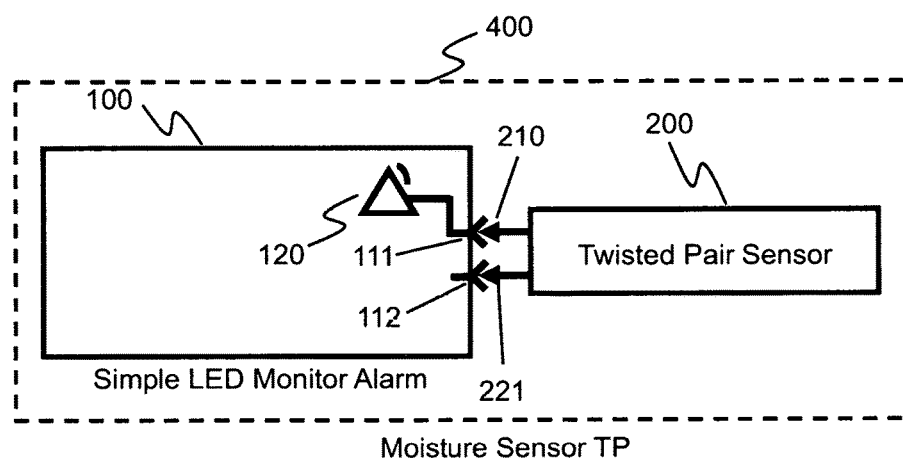
FIG. 4 is a simple moisture alarm monitor activating the alarm in the presence of moisture.

Referring to FIG. 4 Moisture Sensor TP 400 with simple monitor alarm 100 connected to twisted pair sensor 200 at connectors 111 and 112 with a two (2) pin connector 210 and 221. Alarm 120 in Moisture Sensor TP 400 is off due to the high resistance between connectors 111 and 112 and insufficient current flowing through the sensor alarm to activate alarm 120. In the event twisted pair sensor 200 is exposed or penetrated with moisture, insulation on wire 220 will dissolve resulting in wires 210 and 220 shorting at 230 in FIG. 2b. The low resistance short circuit at 230 results in current flowing through the simple monitor alarm 100 activating alarm 120 in Moisture Sensor TP 400 indicating to the user the presence of moisture at twisted pair sensor 200.

Figure 3B:
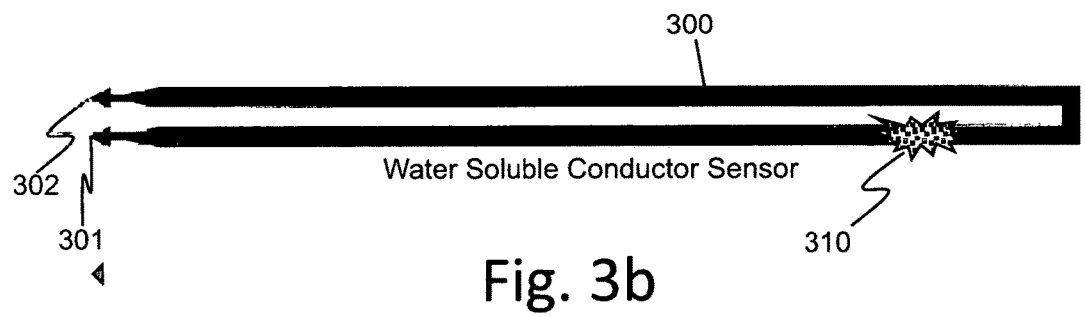
FIG. 3b is a water soluble electric conductor using a soluble material doped with carbon or metal such as silver for conductivity with a portion dissolved by moisture creating an open circuit.
Figure 5:
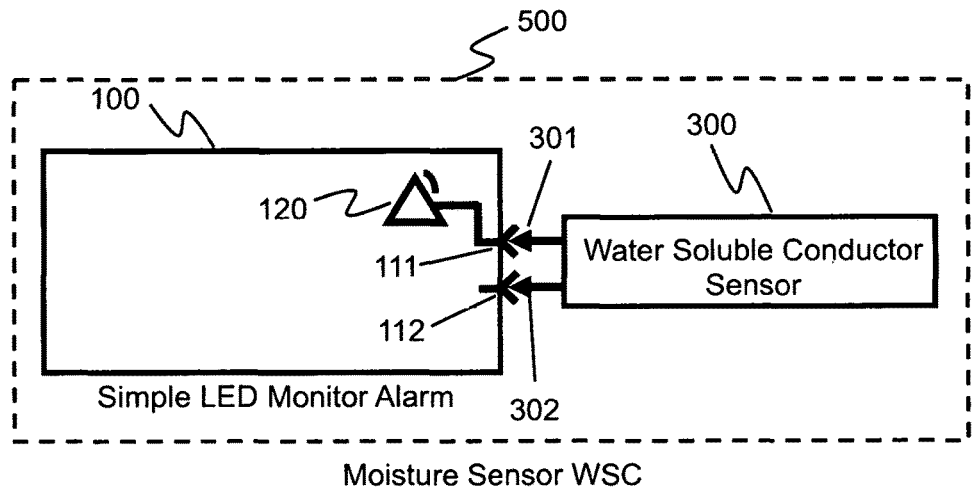
FIG. 5. is a simple moisture alarm monitor with an alarm turns off (de-activate) in the presence of moisture.

FIG. 5 depicts another embodiment of the invention using water soluble conductor 300 attached to simple sensor alarm 100 identified as Moisture Sensor WSC 500. Moisture Sensor WSC 500 alarm 120 activates at the time water soluble conductor 300 is mated or plugged into connector 111 and 112. Moisture Sensor WSC 500 with alarm 120 on indicates to the user the Moisture Sensor WSC 500 is operational and functional. In the event the water soluble conductor 300 is penetrated or exposed to moisture, the conductor dissolves and the conductive particles disperse as indicated in FIG. 3b at 310 creating an open conductor or high resistance conductor. The resistance at connector 301 and 302 reducing the current through sensor alarm 100 de-activating alarm 120 of Moisture Sensor WSC 500.

Figure 6:
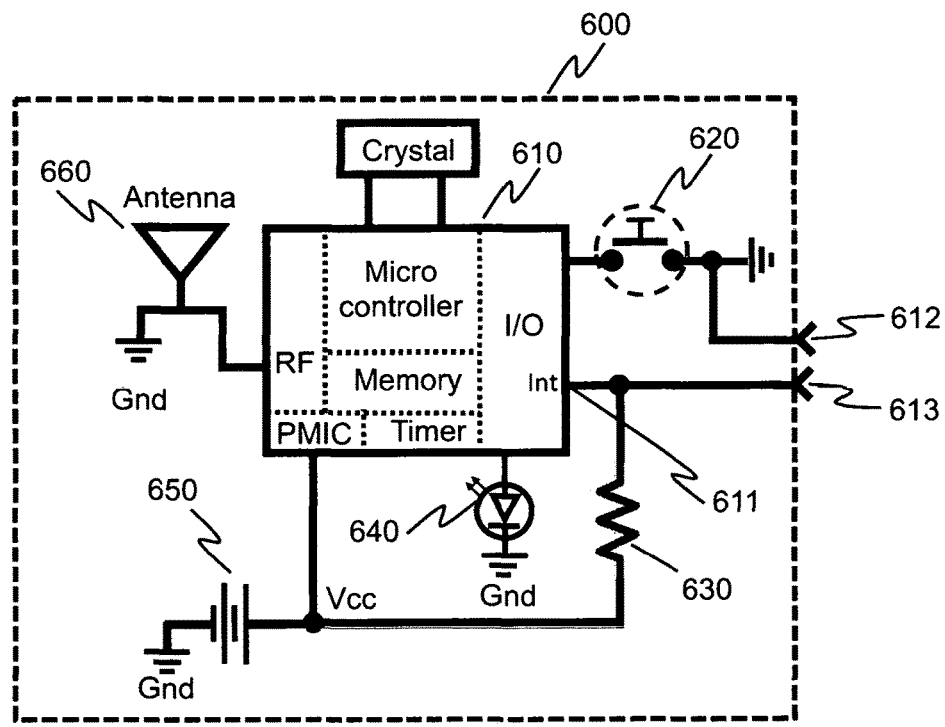
FIG. 6 is a block diagram of a wireless moisture monitor.

A preferred embodiment of the invention is depicted in FIG. 6. block diagram of a wireless moisture monitor capable of monitoring a moisture sensor and transmitting the status of the moisture sensor to a supervisor system controlling multiple wireless moisture monitors. Microcontroller 610 incorporating memory for storing executable code, user parameters, and user data where the executable code manages the PMIC (Power Management Integrated Circuit), timer (watchdog timer), RF, and I/O sections. The wireless moisture monitor 600 is designed to operate for a period greater than 12 months using a single 3 volt 165 mAh button battery 650 to keep the size and weight of the wireless moisture monitor 600 to a minimal. The interrupt pin 611 is active in a low power state monitoring the moisture sensor and the watchdog timer is operational and counting while the remaining microcontroller 610 circuits are inactive.

Wireless Moisture Monitor 600 connects with contacts 612 and 613 to mate with the moisture sensors such as twisted pair sensor 200 connector 211 and 222 or water soluble conductor sensor 300 connector 302 and 301. Resistor 630 provides a voltage bias to microcontroller interrupt pin 611 to Vcc when twisted pair sensor 200 is connected. In the event twisted pair sensor 200 is exposed to moisture resulting in a short between 211 and 222 pins pulling interrupt pin 611 to ground triggering the interrupt routine 710 FIG. 7 executing code for the wake up at routine 712.

With the water soluble conductor sensor 300 connected to the wireless moisture monitor 600 pulls the bias resistor input pin 611 to ground with little or no resistance between pins 302 and 301 connected to pins 612 to 613 through the water soluble conductor sensor 300. When water soluble conductor sensor 300 is exposed to moisture and the conductive material disperses 310 creating an open circuit or high resistance circuit between pins 612 and 613 inputs to the wireless moisture monitor 600 resulting in interrupt pin 611 to increase from ground to Vcc triggering interrupt routine 710 FIG. 7 and executable code initiates wake up routine 712 FIG. 7.

Microcontroller 610 interrupt pin 611 is programmed to be normal non-inverting for connecting twisted pair sensor 200 and inverting for water soluble conductor sensor 300.

Figure 7:
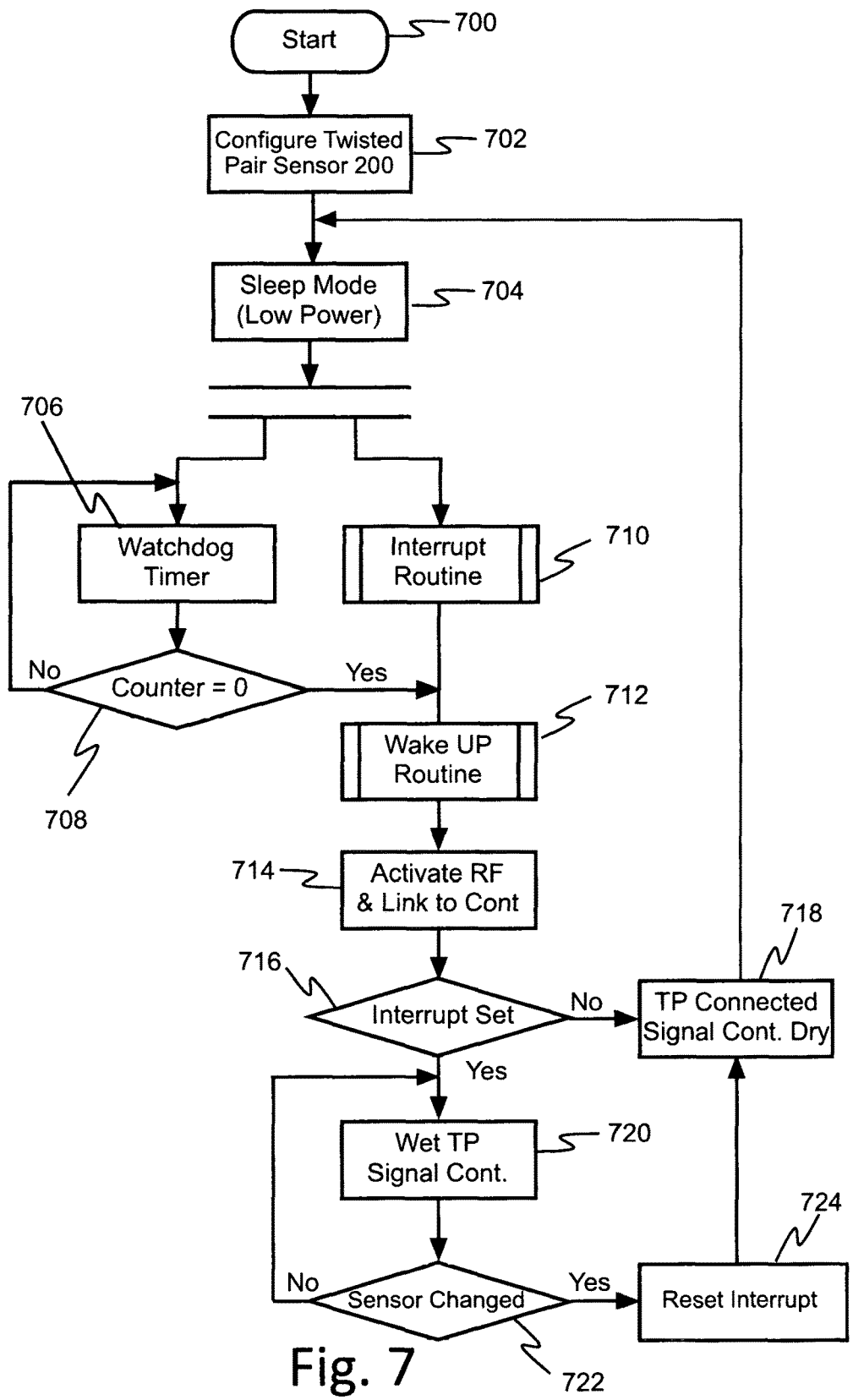
FIG. 7 a flow diagram for the wireless moisture monitor.

The FIG. 7 software flow chart starts at 700 and moves to 702 configuring microcontroller 610 interrupt input 611 to be non-inverting for connecting to the twisted pair sensors 200. The watchdog timer is started at 706 and counts down a predetermined amount of time and when the watchdog timer is zero as detected at 708, executable code moves to wake up routine 712 where the code activities the microcontroller 610 PMIC to power up microcontroller 610, RF, and I/O sections of circuitry.

Figure 8:
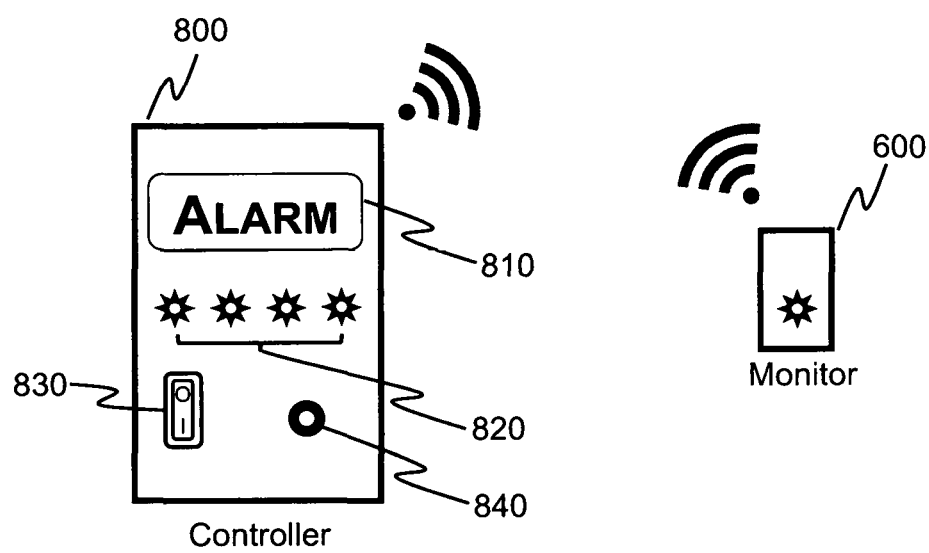
FIG. 8 depicts a system showing the wireless moisture monitor and controller.

Concurrently with watchdog timer operating, the microcontroller 610 circuitry, is monitoring interrupt pin 611 for a change from Vcc to a value less than the input threshold value indicating the moisture sensor has been penetrated with moisture triggering the executable code to enter wake up routine 712. Software starts Power Management Integrated Circuit (PMIC) to power up the microcontroller 610, I/O section, RF, and Memory. The RF communications link to a controller 800 FIG. 8 is establish at 714 notifying the controller 800 the wireless moisture monitor 600 is active and operational.

Routine 716 could have been reached due to the Watchdog Timer 706 counting down to zero at 708 without setting interrupt at 710. Watchdog timer 706 software routine is designed to provide the controller 800 the status of wireless moisture monitor 600 has moisture sensor 200 or 300 connected and void of moisture. Executable code initiates 718 signaling the controller 800 through the RF section the moisture sensor is connected and dry after which returns to 704 placing the microcontroller 610 in sleep mode and restarting watchdog timer 706.

Figure 2B:
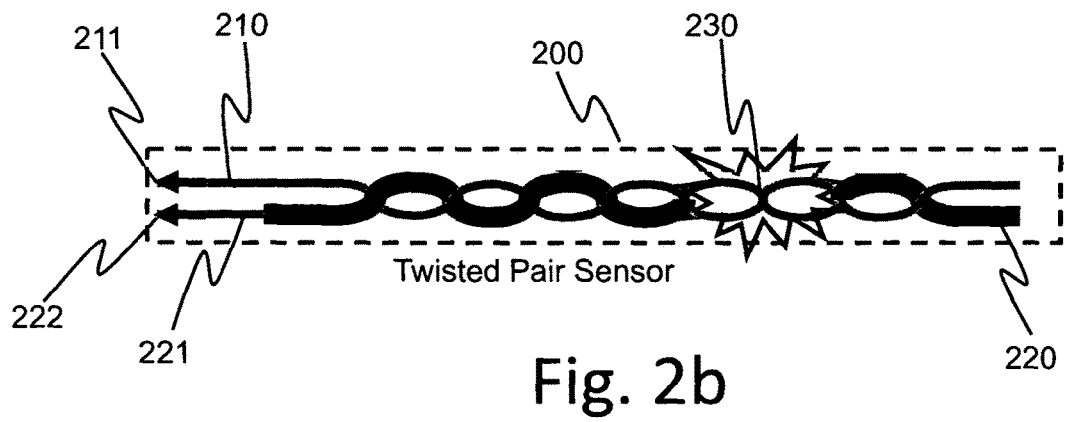
FIG. 2b is water soluble insulation coated wire twisted together with a portion dissolved by moisture results shorting the wires together.

When twisted pair sensor 200 has been exposed to moisture and the water soluble insulated coating is dissolved as shown FIG. 2b 230 on wire 220, resulting in a short or low resistance connection 230 connected through connector 222 to 613 pulling microcontroller 610 interrupt pin 611 down to a value less than the input threshold triggering and activating interrupt routine 710. Interrupt is set indicating moisture sensor has been penetrate by moisture and executable code starts the wake up routine 712 powering up the microcontroller 610 and activates RF and link to controller 800 at 714.

Interrupt Routine 710 sets interrupt and the executable code moves through interrupt set 716 signal the controller 800 at 720 the moisture sensor is wet or penetrated by moisture. Executable code will routinely signal controller 800 of a wet sensor until the sensor has been replaced by a dry sensor 722. Once executable code finds sensor changed 722, the interrupt is reset at 724 and the executable code signals the controller 800 the moisture sensor is dry and operational 718. Executable code returns to sleep mode routine 704 and starts the watchdog timer 706 with a dry moisture sensor and monitoring pin 611 for executing the interrupt routine 710 in the event of liquid penetration of the moisture sensor.

FIG. 8 shows the moisture sensor system with the monitor 600 connected to twisted pair sensor 200 or soluble conductor 300 and with a RF connection to controller 800. Controller 800 is a computing device with a processor, display 810, memory, executable code, input/output, LED status panel 820 and RF communications including Wi-Fi, Bluetooth and/or other RF protocols used for digital communications such as executable code downloads including updates in addition to user specific parameters including software code to manage the monitor 600. Controller 800 displays the system status on display 810 and/or LEDs 820 including sensor disconnected, sensor wet, monitor 600 low battery alarm, monitor 600 communications channel lost and/or controller 800 operating on emergency power (battery) as provisioned by the supervisor system communicating with the supervisory system. Switch 620 programmed during the provisioning of microcontroller 610, can be programmed as a reset button to restart the microcontroller 610 in the event of a software failure or switch 620 can be programmed to aid in pairing the wireless moisture monitor 600 with the controller 800 or a variety of other functions.

Controller 800 is designed to provision and operate one or more monitors 600 while communicating with a supervisor system receiving provisioning information for each of the monitors 600 and receiving monitor 600 status and displaying on controller 800 while transmitting the data to the supervisory system.

It is obvious to one skilled in the art, the controller 800 could be any computing device with a bluetooth communications system including iPhone, Android, Microsoft, tablets and computers. Controller 800 can be programmed to operate the monitor 600 initiating a status request, placing the monitor 600 in sleep mode to name a few operations.

What is claimed is:

1. A wireless moisture monitor comprising:
    a monitor microcontroller programmed with instructions for monitoring a connected moisture sensor;
    said moisture sensor comprises a soluble conductive material, wherein the soluble conductive material dissolves in the presence of moisture such that, the conductive elements become dispersed resulting in high resistance; and
    said moisture sensor transition to high resistance activates interrupt software and RF transceiver;
    monitor microcontroller initiate a wireless transmission to the controller communicating said moisture sensor is wet;
    said monitor microcontroller monitoring said moisture sensor looking for an open circuit indicating said moisture sensor has been replaced;
    said monitor microcontroller transmits to controller said moisture sensor has been changed and is dry;
    said monitor microcontroller software activates interrupt and places monitor microcontroller circuits in lower power sleep mode.

2. A moisture sensor system that monitors for moisture penetrating a material comprising:
    a moisture sensor electrically connected to a monitor microcontroller interrupt circuit;
    said monitor microcontroller monitors interrupt input in a low power sleep mode of operation;
    said moisture sensor, wherein the sensor comprises a soluble conductive material, wherein the soluble conductive material dissolves in the presence of moisture dispersing conductive elements resulting an electrical high resistance triggering the monitor microcontroller interrupt software routine;
    the software initiates a RF transmission repeatedly signaling a wet sensor to the controller until said sensor is replaced with a dry sensor; and
    the software signals the controller with RF transmission the sensor has been replaced and the monitor is operational; and
    said software returns the monitor microcontroller to monitoring the interrupt in a low power sleep mode.

* * * * *